United States Patent
Ferrera et al.

(10) Patent No.: US 6,240,231 B1
(45) Date of Patent: May 29, 2001

(54) VARIABLE STIFFNESS FIBER OPTIC SHAFT

(75) Inventors: David A. Ferrera, Manhattan Beach; Nicholas C. Debeer, San Francisco; Thuzar Han, Fremont; Daniel R. Kurz; Rose Y. Wong, both of Sunnyvale, all of CA (US)

(73) Assignee: Micrus Corporation, Mountain View, CA (US)

( * ) Notice: Subject to any disclaimer, the term of this patent is extended or adjusted under 35 U.S.C. 154(b) by 0 days.

(21) Appl. No.: 09/219,572

(22) Filed: Dec. 22, 1998

Related U.S. Application Data

(63) Continuation-in-part of application No. 08/996,053, filed on Dec. 22, 1997, now abandoned.

(51) Int. Cl.[7] .............................. G02B 6/04; A61B 18/22
(52) U.S. Cl. .................. 385/115; 600/433; 604/604; 604/607; 606/15; 606/16
(58) Field of Search .................... 600/433–435; 604/280, 281; 385/115, 117, 118, 128; 606/15, 16

(56) References Cited

U.S. PATENT DOCUMENTS

| | | |
|---|---|---|
| Re. 31,855 | 3/1985 | Osborne . |
| 3,417,746 | 12/1968 | Moore et al. .................. 600/184 |
| 3,485,234 | 12/1969 | Stevens . |
| 3,670,721 | 6/1972 | Fukami et al. .................. 600/140 |
| 3,788,304 | 1/1974 | Takahashi .................. 600/141 |
| 4,176,662 | 12/1979 | Frazer .................. 128/6 |
| 4,241,979 | 12/1980 | Gagen et al. .................. 385/107 |
| 4,690,175 | 9/1987 | Ouchi et al. .................. 138/131 |
| 4,753,222 | 6/1988 | Morishita .................. 600/140 |
| 4,753,223 | 6/1988 | Bremer .................. 128/4 |
| 4,904,048 | 2/1990 | Sogawa et al. .................. 385/118 |
| 4,969,709 | 11/1990 | Sogawa et al. .................. 385/118 |
| 4,976,690 | 12/1990 | Solar et al. .................. 604/103.06 |
| 5,037,404 | 8/1991 | Gold et al. .................. 604/282 |

(List continued on next page.)

FOREIGN PATENT DOCUMENTS

| | | |
|---|---|---|
| 680041 | 6/1992 | (CH) . |
| WO 87 02473 | 4/1987 | (WO) . |

*Primary Examiner*—Rodney Bovemick
*Assistant Examiner*—Juliana K. Kang
(74) *Attorney, Agent, or Firm*—Fulwider Patton Lee & Utecht, LLP

(57) ABSTRACT

The variable stiffness optical fiber shaft includes a optical fiber, and at least one coaxial layer of heat shrink polymer disposed over the optical fiber of a length shorter than the optical fiber, to provide variations in stiffness along the length of the shaft. The variable stiffness optical fiber shaft preferably includes a plurality of coaxial layers of heat shrink polymer encapsulating the optical fiber, extending from the proximal end of the optical fiber toward the distal end, the plurality of coaxial layers having different lengths to provide said optical fiber shaft with varying stiffness over the length of the optical fiber shaft. The plurality of coaxial layers can be arranged in successive progressively shorter coaxial layers, and can be formed of heat shrink polymeric material, such as polyethylene, PTFE, PEEK, PET or PPS. The variable stiffness optical fiber shaft can also include a coaxial strain relief member disposed over the outer coaxial polymer layers at the proximal end, and a connecting hub disposed over the strain relief member. The variable stiffness optical fiber shaft can also include a hypo tube attached to the optical fiber, and a reinforcing braid attached over the optical fiber, as well as a radiopaque marker that can be a reinforcing coil. A shape memory collar can also be attached over the distal end of the optical fiber, with a distal sheath extending over a portion of the shape memory collar. A hub can also be attached over the proximal portion of the optical fiber. A method of constructing the variable stiffness optical fiber shaft is also provided.

30 Claims, 7 Drawing Sheets

U.S. PATENT DOCUMENTS

| | | | |
|---|---|---|---|
| 5,129,890 | 7/1992 | Bates et al. . | |
| 5,213,111 | 5/1993 | Cook et al. . | |
| 5,217,440 | 6/1993 | Frassica | 604/524 |
| 5,228,453 | 7/1993 | Sepetka . | |
| 5,243,996 | 9/1993 | Hall . | |
| 5,251,640 | 10/1993 | Osborne . | |
| 5,308,342 | 5/1994 | Sepetka et al. | 604/525 |
| 5,358,493 | 10/1994 | Schweich, Jr. et al. | 604/264 |
| 5,423,773 | 6/1995 | Jimenez | 604/282 |
| 5,437,632 | 8/1995 | Engelson | 604/53 |
| 5,443,478 | 8/1995 | Purdy . | |
| 5,484,424 | 1/1996 | Cottenceau et al. | 604/525 |
| 5,499,973 | 3/1996 | Saab | 604/96.01 |
| 5,507,995 | 4/1996 | Schweich, Jr. et al. | 264/293 |
| 5,514,128 | 5/1996 | Hillsman et al. . | |
| 5,531,685 | 7/1996 | Hemmer et al. | 604/95.05 |
| 5,533,985 | 7/1996 | Wang | 604/264 |
| 5,536,235 | 7/1996 | Yabe et al. | 600/121 |
| 5,549,109 | 8/1996 | Samson et al. | 600/381 |
| 5,605,162 | 2/1997 | Mirzaee et al. | 128/772 |
| 5,622,665 | 4/1997 | Wang | 264/150 |
| 5,643,251 | 7/1997 | Hillsman et al. | 606/7 |
| 5,649,909 | 7/1997 | Cornelius | 604/96 |
| 5,653,691 | 8/1997 | Rupp et al. | 604/96 |
| 5,662,622 | 9/1997 | Gore et al. | 604/282 |
| 5,666,968 | 9/1997 | Imran et al. . | |
| 5,700,253 | 12/1997 | Parker | 604/526 |
| 5,711,909 | 1/1998 | Gore et al. | 264/320 |
| 5,733,400 | 3/1998 | Gore et al. | 156/158 |
| 5,759,173 | 6/1998 | Preissman et al. | 604/96 |
| 5,769,828 | 6/1998 | Jonkman | 604/526 |
| 5,782,809 | 7/1998 | Umeno et al. | 604/280 |
| 5,788,653 | 8/1998 | Lorenzo | 600/585 |
| 5,792,124 | 8/1998 | Horrigan et al. | 604/282 |
| 5,797,842 | 8/1998 | Pumares et al. | 600/435 |
| 5,807,354 | 9/1998 | Kenda | 604/280 |
| 5,876,373 * | 3/1999 | Giba et al. | 604/95 |
| 5,954,651 * | 9/1999 | Berg et al. | 600/434 |

* cited by examiner

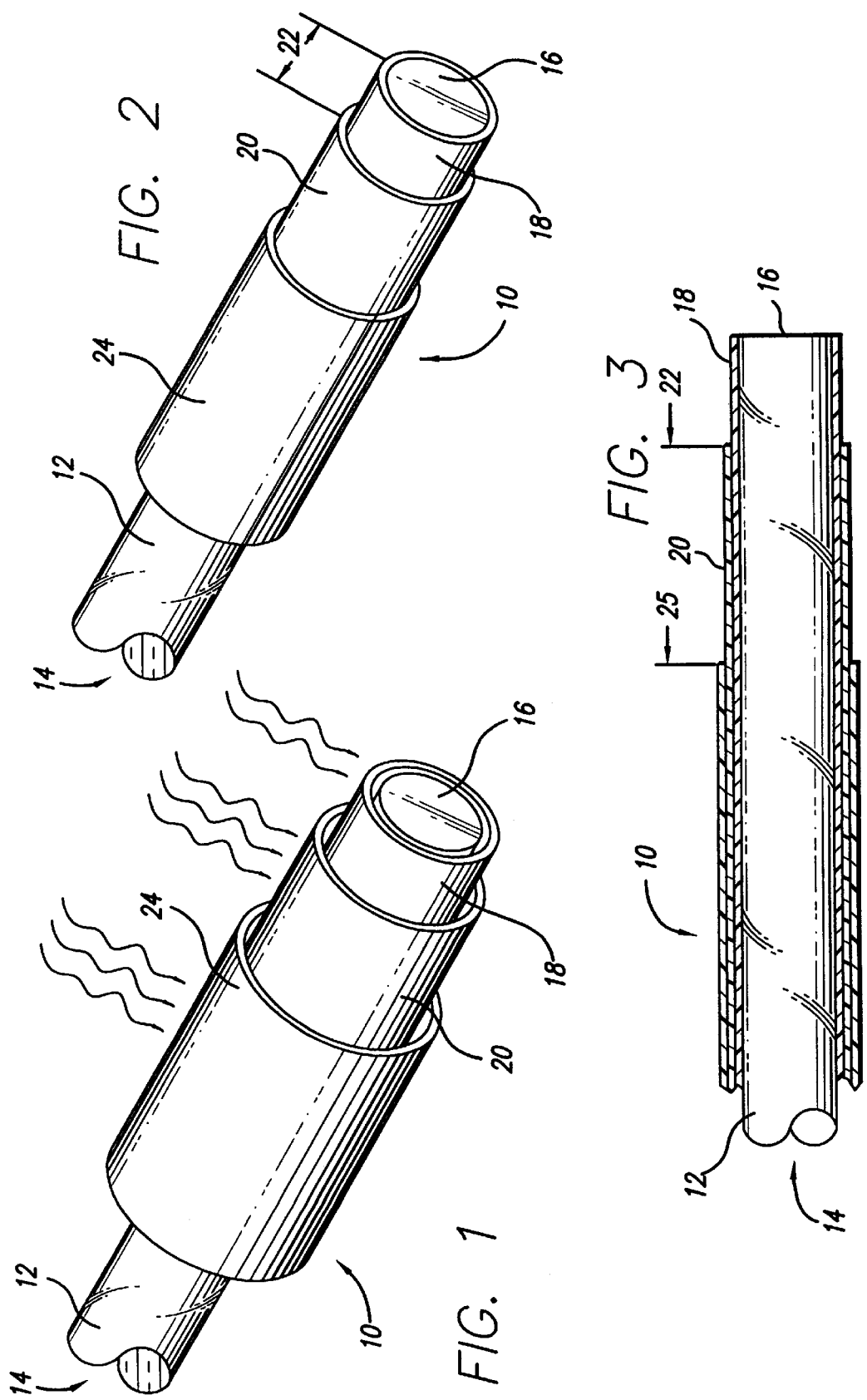

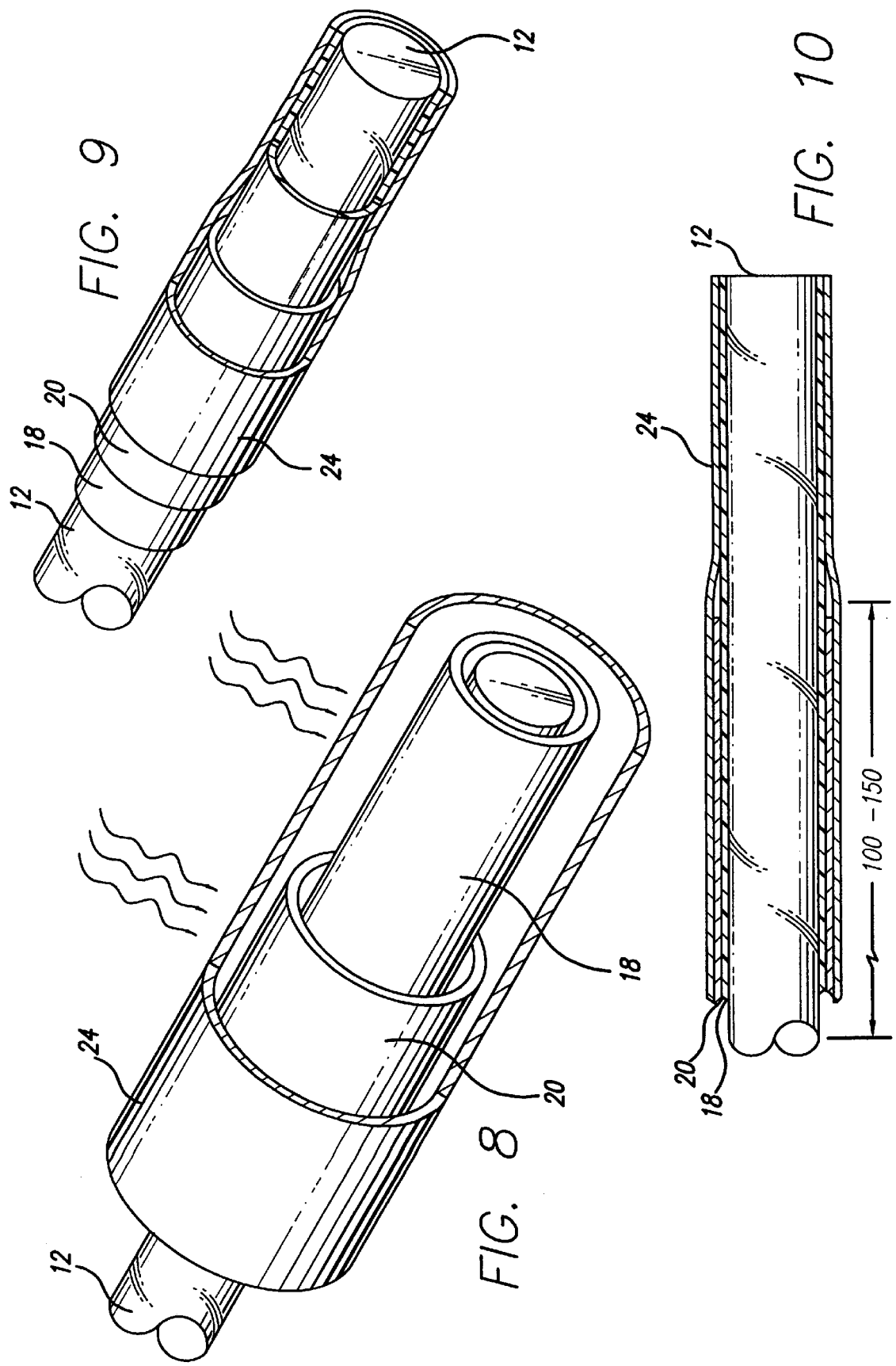

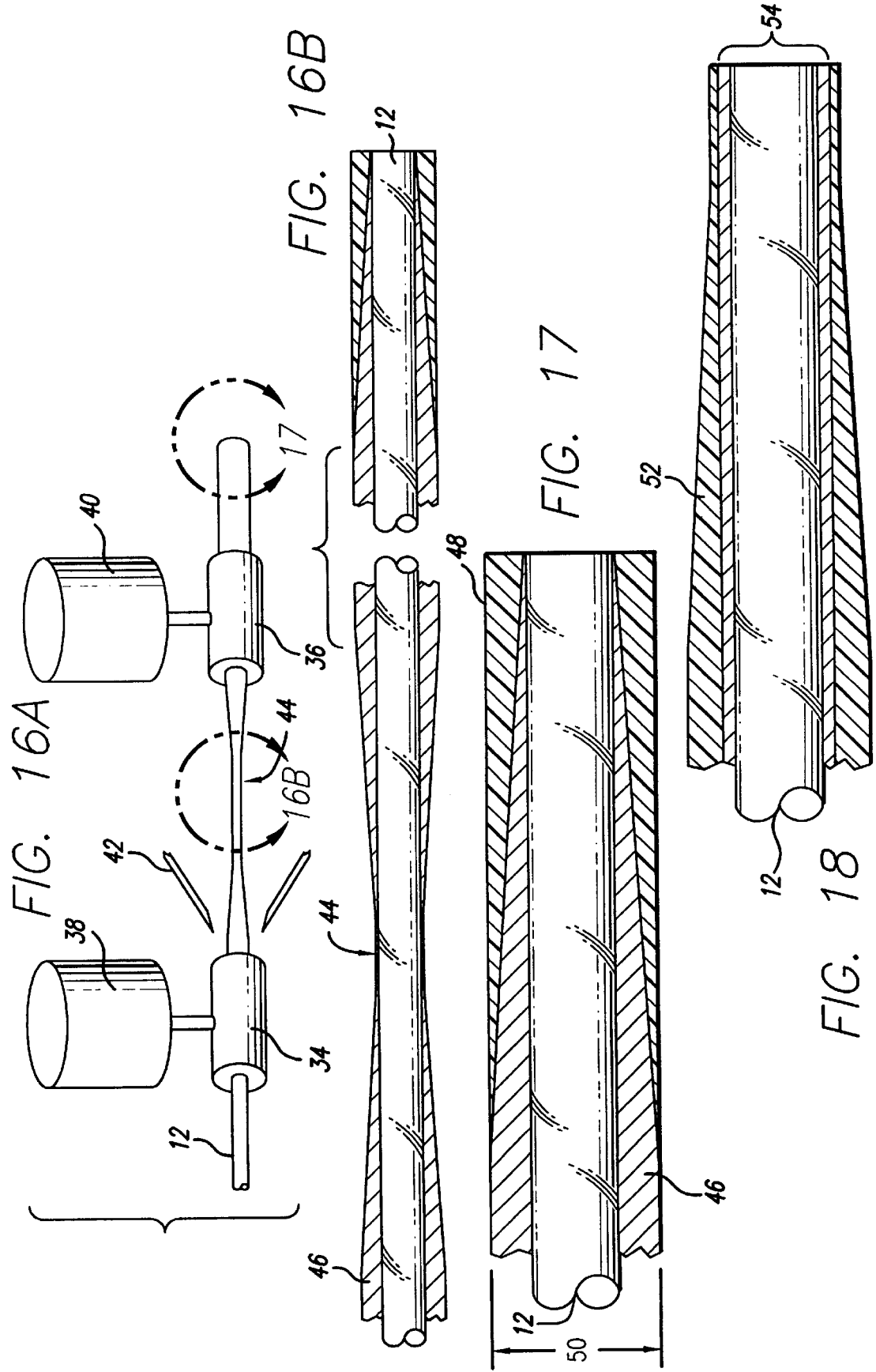

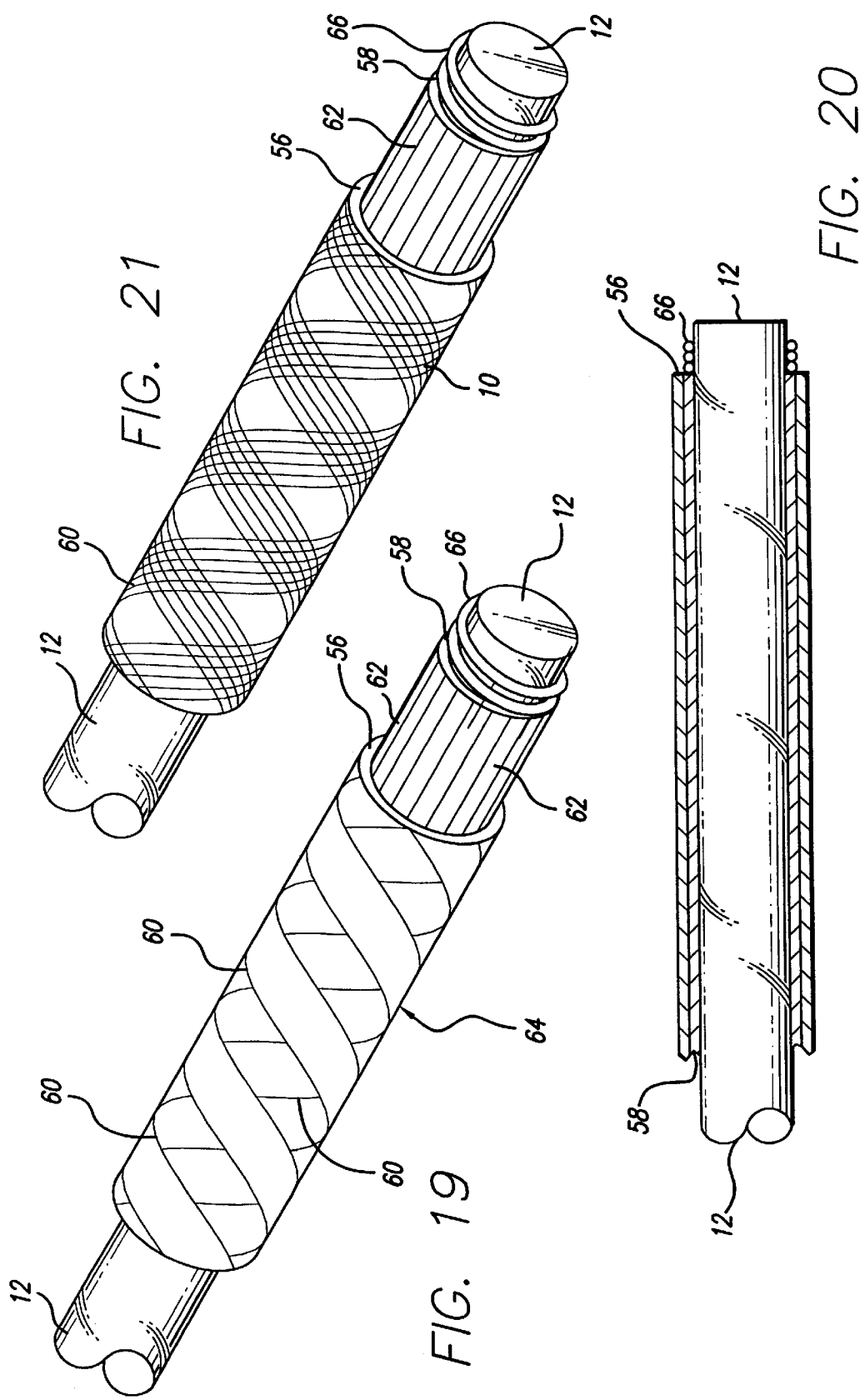

VARIABLE STIFFNESS FIBER OPTIC SHAFT

RELATED APPLICATIONS

This is a continuation-in-part of Ser. No. 08/996,053 filed Dec. 22, 1997, now abandoned.

FIELD OF THE INVENTION

This invention relates generally to interventional medical devices, and more particularly concerns an optical fiber composite shaft having variable stiffness for enhanced performance of the composite shaft when used with or without a guide catheter, or as a stand-alone flow directed device for use in the vascular system as part of an imaging system, a therapeutic system, or for delivery of medical devices.

DESCRIPTION OF RELATED ART

Conventional minimally invasive catheter based therapies typically require guide wires that are one to two meters long extending through a longitudinal lumen in the catheter, and that are torqueable and pushable at the proximal end, yet soft and flexible at the distal end. Many such guidewires are made of stainless steel or the like, and are ground to tapers which provide the desired bending properties along the guidewire. Recently, numerous minimally invasive sensing and actuation procedures have been developed which benefit from the unique qualities of an optical fiber to deliver optical light or power to the distal tip of the optical fiber. For example, optical fiber based technology can be used for imaging, treatments such as "thrombolyzing" blood or cutting tissue by use of high energy light delivered through the end of the optical fibers, and for the delivery of therapeutic agents, such as timed release agents or embolics. However, conventional optical fiber technology has not been easily adaptable to such applications, particularly when the optical fiber must also act as a guidewire, either within a catheter or as a stand-alone device, since optical fibers, when used alone, are not very torqueable, pushable or resilient when compared to guide wires made from a variety of other, more rigid, materials. Also, small diameter optical fibers are quite "floppy", while larger diameter fibers can be too stiff to maneuver through sharp bends, and the use of optical fibers as guidewires or pushers within catheters can thus be difficult and quite technique sensitive.

A variable stiffness catheter having a longitudinal lumen is known that is composed of a relatively flexible outer coaxial tube and at least two tandemly disposed inner coaxial tube segments, the tube segments varying in stiffness, with the stiffest being located at the proximal end of the catheter and the least stiff ending proximal of the distal end of the catheter, thus providing the catheter with a minimum of two regions of different stiffness and flexibility. In order to reinforce a wide variety of catheters incorporating longitudinal lumens for interventional therapies, catheters in the prior art have used reinforcements to the exterior of the catheter, including additional strengthening layers and the like to alter the bending characteristics of the catheter. However, such a catheter structure is typically only capable of being used with a guidewire, and thus cannot provide the benefits of optical fiber technology unless the guidewire is withdrawn and exchanged for an optical fiber. Thus, there remains a serious limitation in the capability of flow directed optical fiber shafts and optical fibers used within catheters to provide the torquability, pushability and resistance to fracture available from metal guidewires. It would also be desirable to provide an optical fiber with variable stiffness to allow optical fibers to be more pushable at the proximal end and more trackable at the distal end, and to make the use of optical fibers in catheter-based therapies more straight forward and less technique sensitive. The present invention addresses these and numerous other needs.

SUMMARY OF THE INVENTION

Briefly, and in general terms, the present invention in its broadest aspect provides for a variable stiffness composite sensor shaft, with a variable stiffness jacket encapsulating the sensor shaft to make the use of such a sensor shaft in catheter based therapies more predictable, straight forward, and less technique sensitive. Typically, such a sensor shaft can be an optical fiber or the like which by itself has physical characteristics that are undesirable for guidewires or stand-alone flow directed devices. By use of the invention, a variable stiffness shaft can be made which is more pushable at the proximal end and more trackable at the distal end, with the capability to provide a wide range of predictable variations in stiffness and other structural parameters over the length of the shaft. It has been found that it is often the case that a sensor shaft such as an optical fiber or ultrasonic conductor is made of a material that has undesirable characteristics for guidewires, since they are generally of a less resilient and strong material than those typically chosen for guidewires. The invention overcomes these limitations by providing for means to selectively strengthen the sensor shaft by low profile overlays of materials to create a composite shaft. A variable stiffness optical fiber shaft constructed according to the invention can be used in conjunction with a guide catheter or as a flow directed, stand alone catheter.

By using the construction according to the invention, coating or heat shrinking a heat shrinkable material on the outside diameter of the optical fiber will improve tracking of the device, and heat shrinking layers of a heat shrinkable material, braid or coil imbedded in a polymer layer, or other polymers in telescoping fashion from proximal to distal end will yield a shaft with a stiffer, more manageable, proximal end and a softer, more maneuverable, distal tip.

The invention accordingly provides in a presently preferred embodiment for a variable stiffness optical fiber shaft for placement within the vascular system, and the invention is particularly adaptable for use within a tortuous, small diameter vessel such as those found in the vasculature of the brain. The variable stiffness optical fiber shaft comprises an optical fiber having a proximal end and a distal end, and at least one coaxial layer of a polymer, metal, or both for providing a desired additional stiffness extending over the optical fiber, to thereby provide desired variations in stiffness along the length of the shaft. In one presently preferred embodiment, the variable stiffness optical fiber shaft comprises a plurality of coaxial layers of heat shrink polymer encapsulating the optical fiber, the coaxial layers extending from the proximal end of the optical fiber toward the distal end, the plurality of coaxial layers having different lengths to provide the optical fiber shaft with varying stiffness over the length of the optical fiber shaft. The plurality of coaxial layers can be arranged in successive progressively shorter coaxial layers, and can be formed of heat shrink polymeric material, such as polyethylene, polytetrafluoroethylene (PTFE) polyethylene terephthalate (PET), polyether ethyl ketone (PEEK), polyphenylene sulfide (PPS), or any of a variety of other polymers which can be fabricated into a structure and necked or shrunk over a shaft. A layer of braid or coil may also be embedded in the polymer to increase the stiffness of the composite shaft in certain areas.

While the invention can effectively use tubes which are placed over the exterior of the optical fiber shaft and then heat shrunk or bonded by adhesive to the fiber, it is also contemplated that the shaft can be reinforced by other longitudinally extending additional structures with varying cross sections for certain specific applications.

In a presently preferred embodiment, the variable stiffness optical fiber shaft comprises a first coaxial layer of a heat shrink polymer extending essentially the entire length of the optical fiber, from the proximal end to the distal end; a second layer of a coaxial layer of a heat shrink polymer, of the same or different material as the first coaxial layer, extending over the first coaxial layer from the proximal end of the optical fiber to a distal position spaced proximally from the distal end of the optical fiber; and a third coaxial layer of a heat shrink polymer, of the same or different material as the first and second coaxial layers, extending over the second coaxial layer from the proximal end of the optical fiber to a distal position spaced proximally from the distal position of the second coaxial layer.

The successive coaxial layers of heat shrink tubing are placed on the fiber extending from the proximal end and ending at different distances from the distal tip of the fiber. Heat can be applied to the successively applied coaxial layers of tubing, resulting in shrinkage of the tubing to encapsulate the fiber, creating a tapered shaft having a variable diameter without edges in the outer surface of the shaft. The tapered structure formed by the successive layers of tubing allows the proximal part of the composite shaft to be relatively stiff, and the distal tip to be flexible and soft. A variety of other techniques can be used within the scope of the invention to accomplish the variable stiffness of the optical fiber shaft. Such techniques include, but are not limited to, the use of a tapered extrusion for the jacket, butt or overlap welding of segments of material with a different stiffness from one another to form the jacket, and use of an adhesively bonded hypo tube of stainless steel or the like as a jacket, possibly with a ground taper to the hypo tube, and braid or coil reinforcing embedded in a polymeric layer.

In another aspect of the invention, the variable stiffness optical fiber shaft further comprises a coaxial strain relief member disposed over the outer coaxial polymer layers at the proximal end of the variable stiffness optical fiber shaft at the proximal end of the optical fiber. The strain relief member is preferably formed of a material and constructed so that the transition in stiffness from the proximal hub to the composite shaft is not abrupt, and can be made of a heat shrink or low durometer elastomeric nylon or Hytrel polymer, such as 25–40 D, for example. The strain relief member is assembled onto the composite shaft by injecting or swabbing an adhesive, such as a UV curable or cyanoacrylate adhesive, over the proximal end of the composite shaft, and by sliding the strain relief member over the proximal end of the optical fiber and coaxial polymeric layers. The outer surface of the polymeric coaxial layers may also be surface treated with a plasma or corona etch process to facilitate the adhesion of the strain relief member to the composite shaft.

In another aspect of the invention, the variable stiffness optical fiber shaft further comprises a connecting hub disposed over the strain relief member and the outer coaxial polymer layers at the proximal end of the variable stiffness optical fiber shaft at the proximal end of the optical fiber for connecting the variable stiffness optical fiber shaft to an optical light source. The proximal hub can be assembled onto the strain relief member and composite shaft by trimming the proximal tip as necessary to square the proximal end of the composite shaft, injecting or swabbing an adhesive, such as an epoxy, a UV curable adhesive, or a cyanoacrylate adhesive, over the proximal end of the strain relief member, sliding the proximal hub over the strain relief member, and allowing the adhesive to cure.

For neurovascular use, the overall length of an optical fiber pusher can be, for example, from 100 to 300 cm, with the outer diameter being less than about 1 French (0.0135 inch). For peripheral use, the overall length of the catheter can be, for example, from 100 to 300 cm, with the outer diameter of the distal 25 to 45 cm being less than about 5 French (0.063 inch), and the outer diameter of the proximal 100 cm being less than about 6 French (0.075 inch). For cardiovascular use, the overall length of the catheter can be, for example, from 150 to 175 cm, with the outer diameter of the distal 25 cm being less than about 3 French (0.038 inch), and the outer diameter of the proximal 100 cm being less than about 4 French (0.050 inch).

In a further presently preferred embodiment of the invention, the basic construction of the optical fiber can be combined with the invention to provide a variable stiffness optical fiber shaft. In practice, optical fibers used for microcoil delivery and the like are approximately 0.003 to approximately 0.014 inches in diameter, with the outer buffer comprising a layer of approximately 0.0005 to 0.002 inches in thickness of a polymer over a thin layer of cladding used to limit the dissipation of light out of the shaft. In one presently preferred embodiment, the outer buffer can be centerless ground to provide a variable thickness characteristic and the fiber can be manufactured with a thicker than normal buffer to facilitate grinding of the buffer to provide a desired bending stiffness either with or without additional layers of stiffening polymers over the outer surface of the fiber.

In still another embodiment of the invention, the reinforcing layer on the outside of the fiber can consist of longitudinal, angled or circumferential windings of high strength fibers which are bonded to the shaft and can be covered by a smooth outer jacket of heat shrink tubing or the like. By use of such a construction, wide variations in stiffness and other physical parameters can be obtained, further extending the uses to which fiber optics or the like can be put in therapeutic minimally invasive procedures.

In still another presently preferred embodiment, the sensor shaft can be subjected to an extrusion process in which at least one polymer is deposited on the exterior of the sensor shaft as it is pulled through extrusion dies. For example, an optical fiber can be drawn through a plurality of such dies, each of them depositing a material of a different hardness on the exterior, with the thickness of the deposit being varied by the speed of the fiber through the die and the temperature of the material being deposited. In this way, tapers to multiple layers can be applied and the overall outside diameter controlled to a desired level. The process can be contained to produce multiple composite shafts in a controlled process, with the shaft cut at desired places to produce individual shafts.

In yet another presently preferred embodiment, the invention provides for a variable stiffness optical fiber shaft for use in interventional therapy, comprising an optical fiber having a proximal end and a distal end; a reinforcing tube attached to the optical fiber, the optical fiber extending therethrough; and a reinforcing braid attached over the optical fiber and preferably over a middle to distal portion of the reinforcing tube. A radiopaque marker can also be attached to the optical fiber; and at least one layer of heat shrink material is attached over the reinforcing tube, the reinforcing braid, the radiopaque marker, and the optical fiber. A shape memory collar is also preferably attached over the distal end of the optical fiber; and a distal protective sheath is attached to the heat shrink material over the distal end of the optical fiber and over a portion of the shape memory collar. In one presently preferred aspect, the optical fiber is covered with an outer buffer, with the outer buffer being removed from a distal portion of the optical fiber. A connecting hub is preferably also attached over a proximal portion of the optical fiber, such as by adhesive, and a strain relief member is also preferably attached over the proximal portion of the optical fiber. In another presently preferred aspect, the reinforcing tube is attached to the optical fiber by adhesive, and has at least one taper ground onto the tube along its length. The reinforcing tube preferably comprises a metal hypo tube that is mechanically locked, bonded, or otherwise fixed, to the optical fiber over at least a portion of its length, and is tapered over at least a portion of its length. In other presently preferred aspects of the invention, the reinforcing braid is formed of stainless steel, the radiopaque marker is attached to the distal portion of the optical fiber, and the radiopaque marker comprises a platinum wire coil. The reinforcing braid may also be formed of a nickel titanium alloy, such as NITINOL, for example. The shape memory collar is also preferably attached over the distal end of the optical fiber by adhesive. In another presently preferred aspect of the invention, the distal sheath is formed of polyethylene, and the distal sheath is attached to the at least one layer of heat shrink material over the distal end of the optical fiber and over a portion of the shape memory collar by adhesive.

In another presently preferred embodiment, the invention provides for a corresponding method of constructing the variable stiffness optical fiber shaft comprising the steps of providing an optical fiber, the optical fiber having a proximal end and a distal end; attaching the reinforcing tube to an optical fiber extending therethrough; applying a reinforcing braid over the optical fiber and over a distal portion of the reinforcing tube; attaching a radiopaque marker; shrinking at least one layer of heat shrink material over the reinforcing tube, the reinforcing braid, the radiopaque marker, and the optical fiber; attaching a shape memory collar over the distal end of the optical fiber; and attaching a sheath to the at least one layer of heat shrink material over the distal end of the optical fiber and over a portion of the shape memory collar. A reinforcing coil over the optical fiber, and in a presently preferred embodiment, the reinforcing coil is applied over a distal portion of the optical fiber and under a distal portion of the reinforcing tube.

Those skilled in the art will also recognize that, while the invention has been described in the context of optical fibers, other, equally non-structural fibers used for therapeutic or measurement purposes may also benefit from the invention.

These and other aspects and advantages of the invention will become apparent from the following detailed description and the accompanying drawings, which illustrate by way of example the features of the invention.

BRIEF DESCRIPTION OF THE DRAWINGS

FIG. 1 is a perspective of a composite shaft of the present invention prior to heat setting.

FIG. 2 is a perspective view of a shaft constructed according to the invention after heat setting of the outer sheaths.

FIG. 3 is a cross section of the shaft of FIG. 2 illustrating a truncated view of the arrangement of the sheaths on the shaft.

FIG. 8 is a perspective view of the unassembled shaft of FIG. 4 prior to heat setting.

FIG. 9 is a perspective of the shaft of FIG. 8 after heat setting.

FIG. 10 is a cross-section of the shaft of FIG. 4.

FIG. 16A is a schematic view of a process for making a composite shaft of the invention.

FIG. 16B is an illustration of the composite shaft at various stages of fabrication.

FIG. 17 is a cross-section of the composite shaft of the invention at 17 of FIG. 16A.

FIG. 18 is a cross-section of an embodiment of a composite shaft of the invention with a tapered outer sheath.

FIG. 19 is a perspective of a further embodiment which includes the arrangement of reinforcing fibers along and about the optical fiber to provide variations in stiffness.

FIG. 20 is a cross-section of the embodiment of FIG. 19.

FIG. 21 is a perspective of a further embodiment showing linearly arranged elements of structural fibers along and about the optical fiber to provide variations in stiffness.

DETAILED DESCRIPTION OF THE PREFERRED EMBODIMENTS

Figure 4:
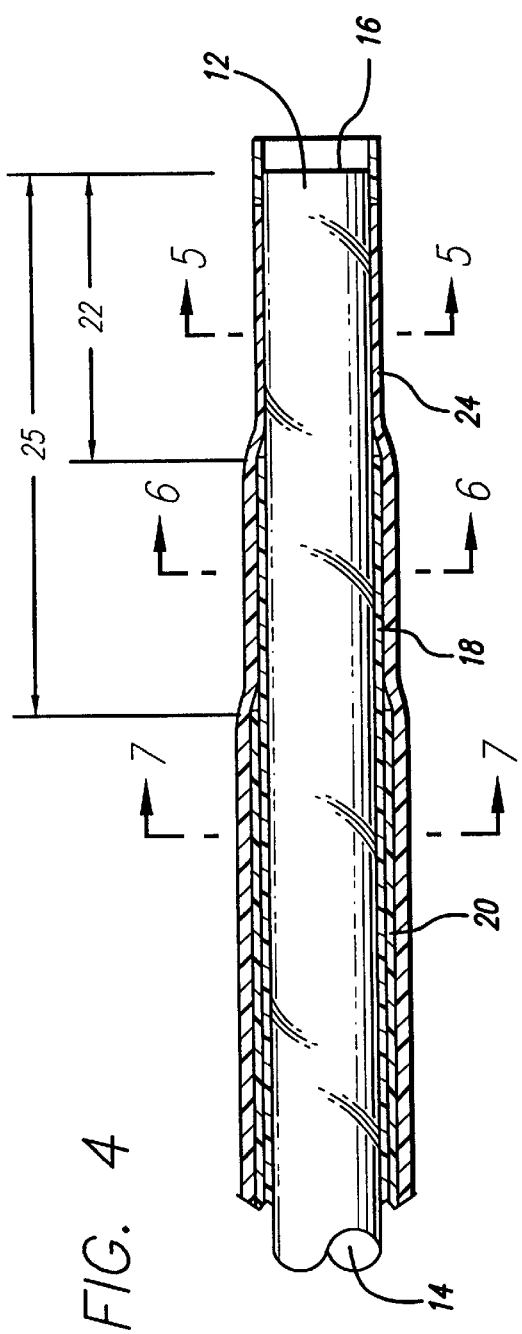
FIG. 4 is an illustration of an alternative embodiment of the invention in which the outer sheath extends over the length of the shaft and terminates in a collar-retainer for a micro-coil.

Modern interventional medical procedures have relied on ever smaller and more flexible devices to reach areas requiring treatment which were previously inaccessible to conventional devices. Among such procedures are the placement of vasoocclusive devices in tiny areas of damaged vasculature such as aneurysms or ruptures in arteries in the brain. Some devices to treat such areas use optical fibers to carry light energy to remote locations at the distal end of the optical fiber. There has been increased uses for such techniques, but certain limits have been found in the use of currently available optical fibers for those purposes.

For example, conventional optical fiber technology has not been easily adaptable to catheter based imaging, treatments such as "thrombolyzing" blood or cutting tissue, or to the delivery of therapeutic agents, such as timed release agents, or embolics, since optical fibers, when used as a stand alone structural device, are not very torqueable, pushable or resilient. Small diameter optical fibers of the type most useful for such therapies frequently can become too floppy, while larger diameter fibers can be too stiff to maneuver through sharp bends, and for these reasons, the use of optical fibers as stand alone guidewires or catheters can be difficult and technique sensitive. Also, since there are practical limits to the diameter of the fiber for specific applications, the use of reinforced guide catheters with longitudinal lumens through which the optical fiber passes can place important restrictions on how small such an assembly can be. Further, if the optical fiber is to be used with both a guidewire and a guiding catheter, there are limits imposed on the techniques that can be employed because of the necessarily larger diameter of such an assembly to accommodate the requirements of the two different shafts within the catheter.

As is illustrated in the drawings, which are provided for the purposes of illustration and not by way of limitation, one preferred embodiment of the invention illustrated in FIGS. 1–3 is embodied in a variable stiffness optical fiber shaft 10 that comprises an optical fiber 12 having a proximal end 14 and a distal end 16, the optical fiber, which may optionally comprise several optical fibers bundled together, and at least one outer polymer layer, the unit generally referred to as an optical fiber, which is sheathed in a first coaxial layer of a heat shrink polymer 18, such as polyethylene, PTFE, PEEK, PET or PPS, for example, although other similar heat shrink polymers may also be suitable. The first coaxial heat shrink layer preferably extends the entire length of the optical fiber, from the proximal end to the distal end.

In the embodiment illustrated in FIGS. 1–3, a second layer 20 of a coaxial layer of a heat shrink polymer can also be provided, that can be made of the same or different material as the first coaxial layer, preferably extending over the first coaxial layer from the proximal end of the optical fiber to a distal position 22 spaced proximally from the distal end of the optical fiber. A third layer 24 of a coaxial layer of a heat shrink polymer, which can be made of the same or different material as the first and second coaxial layers, preferably extends over the second coaxial layer from the proximal end of the optical fiber to a distal position 25 spaced proximally from the distal position 22 of the second coaxial layer. For example, in a variable stiffness optical fiber shaft about 175 cm in length, the second coaxial layer would typically extend 170 cm from the proximal end of the optical fiber, and the third coaxial layer would typically extend about 100 cm from the proximal end of the optical fiber.

Additional coaxial layers of heat shrink polymer can also be placed around the coaxial layers of heat shrink polymer, preferably at the proximal end of the optical fiber and in the same generally progressive telescoping fashion as the first, second and third coaxial layers, although it may also be suitable to place one or more coaxial layers of heat shrink polymer over other sections of the variable stiffness optical fiber shaft to provide variations in stiffness along the length of the shaft as may be appropriate for specific applications. As illustrated in FIGS. 1–3, the process of forming the invention according to this embodiment involves progressively surrounding the central optical fiber 12 with shrink wrap tubing which extends over selected regions of the optical fiber in thicknesses and lengths related to the areas to be stiffened. The assembly is then exposed to heat so that the outer layers shrink down around the optical fiber to thereby form a stiffened shaft assembly.

A connecting hub, such as a bayonet style connector or ANSI threading, for connecting the variable stiffness optical fiber shaft to an optical light source (not shown) can be disposed over the outer coaxial polymer layer at the proximal end of the variable stiffness optical fiber shaft. Similarly, a coaxial strain relief member can also be disposed about the proximal end of the shaft, adjacent to and distal to the connecting hub.

For neurovascular use, the overall length of the catheter can be, for example, from 100 to 300 cm, with the outer diameter being less than about 1 French (0.0135 inch). For peripheral use, the overall length of the catheter can be, for example, from 100 to 300 cm, with the outer diameter of the distal 25 cm being less than about 5 French (0.063 inch), and the outer diameter of the proximal 100 cm being less than about 6 French (0.075 inch). For cardiovascular use, the overall length of the catheter can be, for example, from 90 to 175 cm, with the outer diameter of the distal 25 to 45 cm being less than about 3 French (0.038 inch), and the outer diameter of the proximal 50 to 100 cm being less than about 4 French (0.050 inch). These dimensions are approximate, and in practical terms, depend upon sizes of shrink tubing that are commercially available.

In one example of the method of manufacturing the variable stiffness optical fiber shaft of the invention, the shaft can be assembled by sliding and centering a heat shrink tube first coaxial layer, such as polyethylene, for example, which can be, for example, 200 cm in length, over a optical fiber, which can be, for example, 205 cm long. The ends of the optical fiber are then clamped, and tension is applied to keep the optical fiber taut. The proximal end of the heat shrink tube is placed into the working area of a heat gun, although other means of controllably heating the heat shrink polymeric sheath may be used. The temperature of the heat shrink tube is heated to approximately 650 F, and the rest of the heat shrink tube is heated by sliding the heat gun along the axis of the heat shrink tube at about three inches per second, for example, until the heat gun has traveled the length of the polymeric material and the heat shrink material has encapsulated the optical fiber. This method is repeated for 150 cm and 100 cm lengths of polymeric tubing, and any further heat shrink tubing to be used for varying the stiffness of the optical fiber shaft, until the outside diameter of the shaft is built up to the desired dimensions to yield the desired degrees of stiffness.

The strain relief member is formed of a material and constructed so that the transition in stiffness from the proximal hub to the composite shaft is not abrupt. In one embodiment, the strain relief member is preferably made of a low durometer Nylon or Hytrel polymer, such as 25–40 D, for example. The strain relief member is assembled onto the composite shaft by injecting or swabbing an adhesive, such as a UV curable or cyanoacrylate adhesive, over the proximal end of the composite shaft, and by sliding the strain relief member over the proximal end of the composite shaft and the polyethylene or other type of heat shrink or metal tubing. The polyethylene composite may also be surface treated with a plasma or corona etch process to facilitate the adhesion of the strain relief member to the composite shaft.

The proximal hub can be assembled onto the strain relief member and composite shaft by trimming the proximal tip as necessary, to square the proximal end of the composite shaft, injecting or swabbing an adhesive, such as an epoxy, a UV curable or cyanoacrylate adhesive, over the proximal end of the strain relief member, sliding the proximal hub over the strain relief member, and allowing the adhesive to cure. It should be readily apparent that other proximal hub and strain relief member designs can also be attached to the proximal end of the composite shaft.

Figure 5:
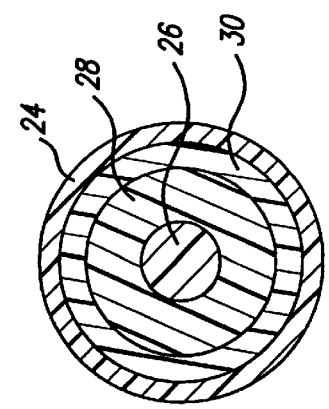
FIG. 5 is the shaft of FIG. 4 at section 5.

FIG. 4 is a cross-section of a second presently preferred embodiment of the invention. In this embodiment, optical fiber 12 has shrink tube layers 18 and 20 disposed at variable distances along the length of the optical fiber from the distal end 16 with the distances at which the layers 18 and 20 terminating distances 22 and 25 being a variable available to the designer to alter the stiffness profile of the optical fiber over its length. The thickness and durometer hardness of the materials, as well as the choice of materials themselves are also available to configure a composite shaft according to the invention which has desired bending stiffness over its length. In this embodiment an outer cover 24 which also may be shrink tubing is laid over the length of the optical fiber from the distal end 16 to the proximal end 14 in order to provide a smooth overall outer sheath and thereby offer the minimum resistance to movement of the optical fiber within a catheter lumen or blood vessel. In such an embodiment the outer layer 24 may be polyethylene, PTFE or other suitable low friction material, consistent with providing the overall bending characteristics desired. FIG. 5 is a cross-section of the shaft according to this embodiment in which the optical fiber 26 is surrounded by a cladding 28 in an outer buffer layer 30 which is then surrounded by the outer sheath 24.

Figure 7:
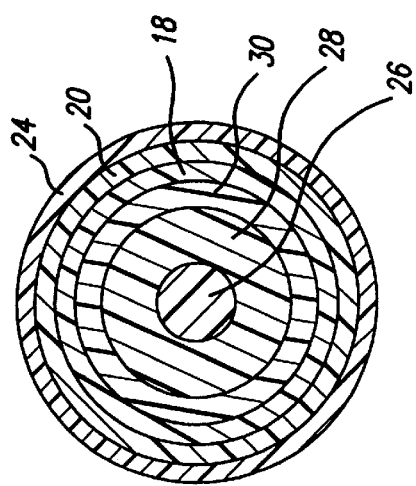
FIG. 7 is the shaft of FIG. 4 at section 7.
Figure 6:
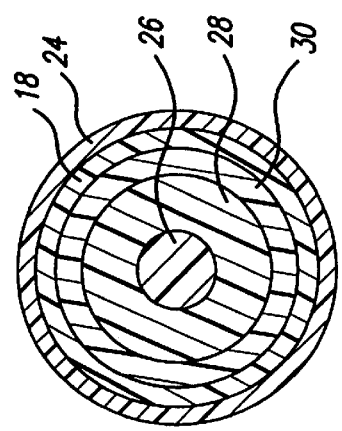
FIG. 6 is the shaft of FIG. 4 at section 6.

FIG. 6 is a cross-section view at 6—6 of FIG. 4 illustrating the construction of FIG. 5 further surrounded by an additional stiffening sheath 18 now within the outer sheath 24. FIG. 7 is a section at 7—7 of FIG. 4 further illustrating an additional stiffening layer 20 within the construction and overlaying layer 18 and within layer 24. While this embodiment has been illustrated in the form of heat shrink tubing, those skilled in the art can recognize that one or more of the layers may also be adhesively bonded either between layers or to the outer layers in order to provide additional desirable characteristics related to shaft stiffness and pushability. In FIGS. 5–7, the optical fiber 12 is shown in cross section to include optical fiber core 26, cladding 28, and the outer buffer 30.

Figure 13:
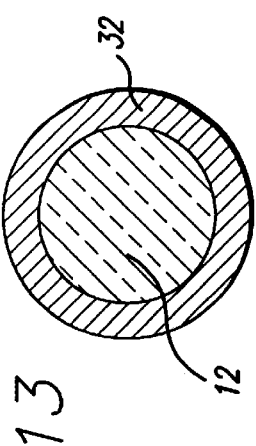
FIG. 13 is a section at 13—13 of FIG. 12.
Figure 14:
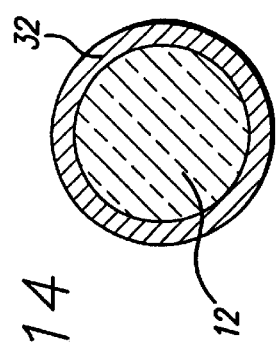
FIG. 14 is a section at 14—14 of FIG. 12.
Figure 15:
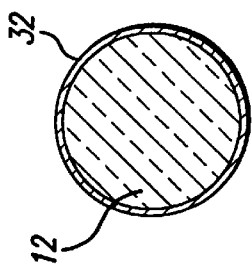
FIG. 15 is a section at 15—15 of FIG. 12.
Figure 11:
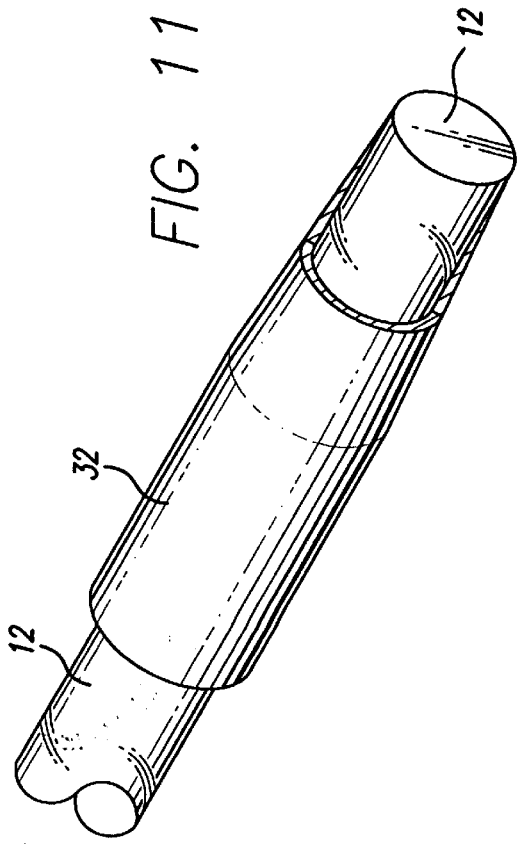
FIG. 11 is a perspective of an alternative embodiment in which the outer cover is tapered by grinding or extrusion to provide a one-piece tapered sheath for the shaft.
Figure 12:
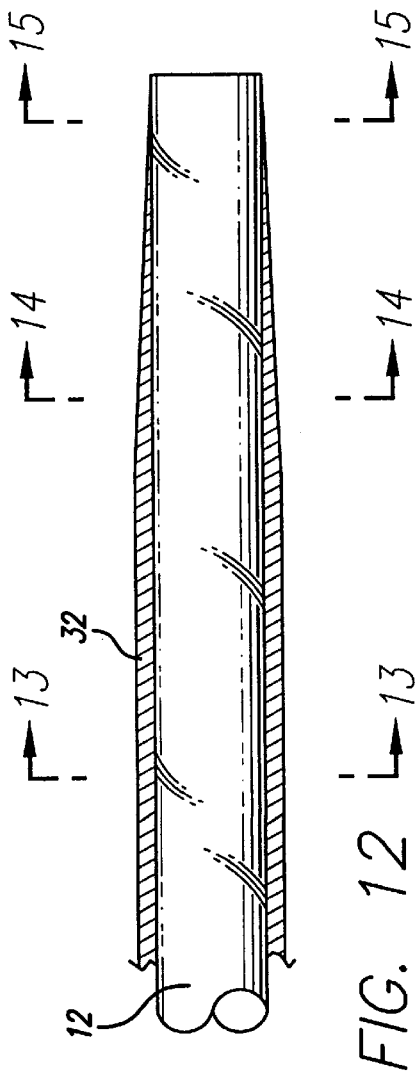
FIG. 12 is a cross-section of the shaft of FIG. 11.

FIG. 8 is a perspective view of the unassembled construction illustrated in FIG. 4. More specifically, outer layer 24 is illustrated as extending over a first inner layer 18 and a second inner layer 20, all of the tubes of this construction overlaying optical fiber 12. When heat and/or tension is applied the structure resulting is as illustrated in FIG. 9 which is a cut-away perspective of the assembled structure of FIG. 4 illustrating the optical fiber 12 closely covered by the outer sheaths 24 and inner sheaths 18, 20, to provide the variable stiffness shaft of the invention. FIG. 10 is a cross-sectional view of the construction resulting from the process and is illustrated in FIG. 9 showing the necking of the outer sheaths upon the ending of the inner sheath at a distance from 100–150 centimeters from the proximal end of the optical fiber element. The invention can also be embodied in a variety of structures which provide variable stiffness over the outer portion of an optical fiber element or the like. FIG. 11 illustrates such an embodiment in which the optical fiber 12 is surrounded by a tube 32 which may be tapered along its length, either in steps or continuously in order to provide a desired stiffness and pushability. Although a variety of methods can be used for such a construction, those known in which are believed to be desirable for various embodiments include centerless grinding of a buffer layer on the outside of the optical fiber, the buffer layer being chosen for its ability to enhance stiffness in variable thicknesses, a tapered hypo tube which is overlaid on the optical fiber and possibly adhesively bonded thereto with the thickness of the hypo tube being varied over its length, and the inclusion of a wire mesh or composite material braid underneath an outer layer shrunken on the shaft where it also can be adhesively bonded to the shaft to provide a further method of increasing torqueability and stiffness to the shaft. Those skilled in the art will also recognize that combinations of the above referenced elements may be used in order to provide a structure with specific and desired combinations of stiffness, torqueability, and pushability over the length of the shaft. FIGS. 13 through 15 illustrate at sections 13—13, 14—14 and 15—15 of FIGS. 12 the change in diameter of the outer tapered layer in the construction described in perspective in FIG. 11 and discussed above.

Those skilled in the art will recognize that a variety of polymers, including those filled with reinforcing fibers or other material may be used to reinforce an optical fiber so that it can be more effectively used as a pusher within a catheter lumen or as a free therapeutic member. For example, the characteristics of the materials to be used may be optimized by use of joining adjacent covers of different materials against one another longitudinally in end to end fashion or overlap to thus provide a constant outer diameter. In such a construction, the outer sheath is formed of joined (by heat and/or pressure) or adhering bonded sections surrounding specific portions of the optical fiber. Similarly, such a construction can be combined with an outer cover to provide a smooth overall exterior to the finished composite shaft.

In another presently preferred embodiment and process of manufacture illustrated in FIGS. 16–18, the optical fiber 12 is drawn through extrusion dies 34 and 36 each of which deposits a plastic material from supply sources 38 and 40 in a controlled manner on the exterior of the fiber. The thickness of the deposit can be controlled by the die configuration, the temperature of the material to be deposited and the speed of the fiber through the dies, or a combination of those parameters. In practice, this construction allows for control of both the outer diameter of the finished shaft and wide variations in the stiffness of the shaft over its length, depending on the material being deposited and the relative thickness of the softer and harder layers. FIG. 16B illustrates a cross section of a composite shaft according to this embodiment, showing the increased tapering of softer and harder portions of the deposited jacket to provide a desired composite shaft during the course of manufacture.

In the process of FIG. 16, an optical fiber 12 is passed at a controlled speed by a feeding mechanism (not shown) through a first die 34 receiving a polymer material from a supply 38 to be deposited on the shaft at a rate controlled by the speed of the shaft through the die. The size of the die and the temperature and composition of the polymer and the speed can be varied to deposit a thicker or thinner layer and to taper the deposit as shown at 44. If desired, quenching jets 42 can be used to cool the polymer after deposit. One or more additional dies 36 can apply a second polymer from supply 40 to create an additional layer of polymer of a different characteristic from the first as illustrated in FIG. 16B.

Using these techniques, a variety of constructions can be created to the composite shaft. FIG. 17 illustrates a composite shaft in which two different polymers 46, 48 are deposited at complimentary rates in successive dies to provide a double tapered cover of consistent outside diameter 50. As an alternative, a single polymer can be deposited in a tapered layer 52 over a shaft to create a tapered composite shaft over the optical fiber 12. Those skilled in the art will recognize that a variety of the above described embodiments can be combined to provide a wide range of desired characteristics to the finished composite shaft.

A further presently preferred embodiment is illustrated in FIGS. 19, 20 and 21, in which overlays 56, 58 of the optical fiber 12 with a layer of woven 60 and/or linearly arranged elements of structural fibers 62 within a matrix are used to create the composite shaft 64. The matrix can be chosen from any of a variety of materials including silicone and the like in order to provide the benefits of the materials without necessarily subjecting the assembly to the undesirable characteristics associated with solid matrices based upon epoxy and polymers. As is illustrated in FIGS. 19, 20 and 21, a reinforcing coil 66, such as a round or flat wire coil, may also be applied over a portion of the optical fiber, to stiffen the optical. The entire assembly can then be enclosed within an outer sheath providing a smooth, low friction cover for the reinforced fiber. Those skilled in the art will recognize that the orientation and composition of the reinforcing strands along and about the shaft can be altered over a wide range to provide any number of desirable characteristics related to pushability, flexibility and stiffness.

Figure 22:
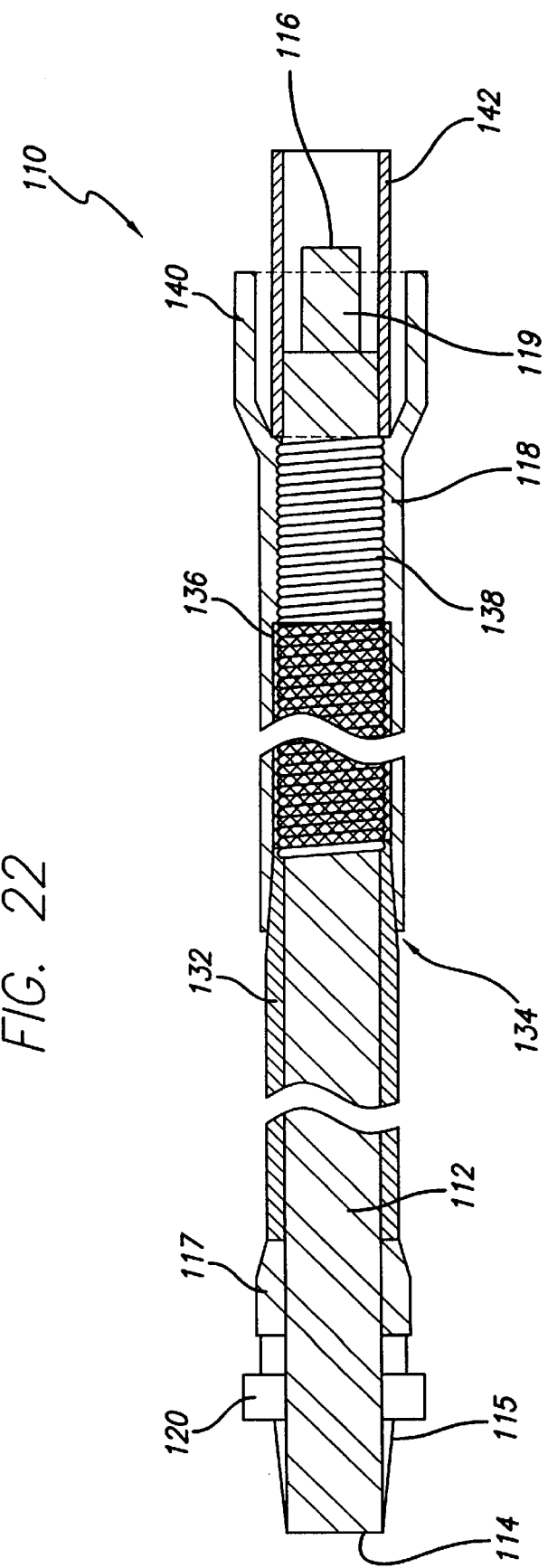
FIG. 22 is cross-sectional view of a further alternate embodiment of a composite shaft illustrating a reinforcing braid, shape memory collar and protective sheath.

In another presently preferred alternate embodiment illustrated in FIG. 22, the invention provides for a variable stiffness optical fiber shaft 110 that comprises an optical fiber 112 having a proximal end 114 with a fiber optic ferrule 115 attached over the optical fiber, and a distal end 116. The optical fiber is preferably of the type that is covered with an outer buffer layer, with the outer buffer layer being removed from a distal portion 119 of the optical fiber, leaving an exposed portion of the optical fiber for improved transmission of light and heat energy to the distal end of the optical fiber shaft. The optical fiber typically includes an optical fiber core and cladding, but may optionally comprise several optical fibers, and at least one outer polymer layer. The unit generally is referred to as an optical fiber, which is covered in a sheath 118 of at least one outer layer of a heat shrinkable polymer, such as polyethylene, PTFE, PEEK, PET or PPS, for example, although other similar heat shrinkable polymers or metallic material may also be suitable. A connecting hub 117 with a bayonet style connector or ANSI threading for connecting the variable stiffness optical fiber shaft to an optical light source (not shown) can be disposed over the outer coaxial polymer layer at a proximal portion of the variable stiffness optical fiber shaft, such as by adhesive, and for example by cyanoacrylate adhesive. Similarly, a coaxial strain relief member 120 can also be attached over the proximal portion of the optical fiber shaft, adjacent to and distal to the connecting hub. a hub attached over a proximal portion of the optical fiber A reinforcing tube 132 is also preferably attached to the optical fiber, to provide stiffness and pushability to the proximal portion of the optical fiber shaft, with the optical fiber extending through the reinforcing tube, such as a metal hypo tube, which can for example be formed of stainless steel or a nickel titanium alloy such as NITINOL, for example, and which may be tapered along its length, either in steps or continuously in order to provide a desired stiffness and pushability. The reinforcing tube preferably has at least one taper 134 ground onto the reinforcing tube along its length to provide a desired taper. Although a variety of methods can be used for such a construction, those known in which are believed to be desirable for various embodiments include grinding of a ground portion 134 of the reinforcing tube over at least a portion of its length, which is overlaid on the optical fiber and possibly adhesively bonded to the optical fiber over at least a portion of its length, such as by cyanoacrylate adhesive, with the thickness of the reinforcing tube being varied over its length.

In another preferred aspect, a reinforcing metal wire mesh braid 136 such as stainless steel, for example, is also attached over a distal portion of the optical fiber, preferably adhesively or mechanically bonded to the optical fiber shaft, and attached over the distal portion of the reinforcing tube, such as by solder, for example, extending underneath an outer layer of heat shrink polymeric material shrunken onto the shaft, to provide torqueability and stiffness to the shaft. The reinforcing braid can alternatively be formed of a reinforcing composite material braid. In another presently preferred aspect, a radiopaque marker 138, such as a platinum wire coil, for example, is attached to the optical fiber, such as at the distal portion of the optical fiber. Other radiopaque materials such as gold or tungsten coils, or the like, may also be suitable. At least one layer of the sheath 118 is preferably attached over the reinforcing tube, the reinforcing braid, the radiopaque marker, and the optical fiber. In addition, the sheath 118 preferably includes an enlarged distal protective sheath portion 140, that extends over a distal shape memory collar 142 formed of shape memory material attached over the distal end of the optical fiber, to thereby restrict the outside diameter of the shape memory material as it retracts. Without such a distal protective sheath portion, the collar of shape memory material, typically having an initial outer diameter of about 0.010 inch, can expand radially when it retracts axially as heat is applied to the shape memory collar to present an outer diameter of 0.016 inch, for example. The inner diameter of the microcatheter through which the optical fiber shaft is delivered is typically only 0.014 inch, so that such a retracted, radially expanded shape memory collar can prevent withdrawal of the optical fiber shaft through the delivery microcatheter. With the distal sheath portion extending over the shape memory collar, the radial expansion of the shape memory collar can be controlled and limited to an outer diameter of 0.013 inch, which will pass through a microcatheter inner diameter of 0.014 inch. The distal protective sheath also serves to minimize cooling effects on the shape memory collar of blood flow during heating of the shape memory collar, while constraining the outside diameter of the recovering shape memory collar during heating, and physically protects the distal tip of the optical fiber shaft. The distal sheath can optionally be tubular, and can be made of any suitable polymeric or metallic material.

The shape memory collar is preferably useful for retaining a distal therapeutic device, such as an embolic coil or stent, for example. The shape memory collar is preferably formed of a shape memory material having a glass transition temperature ($T_g$) above body temperature, such as polyurethane, heat shrink tubing such as polyethylene terephthalate (PET) or high density polyethylene (HDPE), or a shape memory metal such as nickel titanium alloy, such as that available under the trade name NITINOL, for example, that can be heat treated to have shape memory behavior. Utilizing such materials, the shape memory material has a desired stressed configuration at a temperature appropriate for introduction into the body via a catheter, and after placement, will take on a more relaxed, unstressed original shape for releasing the endoluminal therapeutic device. The shape memory collar can be attached to the distal end of the optical fiber by an adhesive, such as cyanoacrylate adhesive, for example.

The variable stiffness optical fiber can be used as a release device for deploying embolic coils at a therapeutic use site. It is also possible to interleave other cylindrical parts between the layers of heat shrink tubing, such as a cylindrical wire mesh braid beneath a layer of shrink wrap to increase torquability and stiffness. With the addition of a polymeric or metallic braid or coil, the device will be much more torqueable and pushable. Non-medical applications for such a construction may include assembly or read-write heads for disk drives and other micro assembly applications.

It will be apparent from the foregoing that while particular forms of the invention have been illustrated and described, various modifications can be made without departing from the spirit and scope of the invention. For example, some of the various techniques of the invention can be advantageously combined for certain applications, while others are effectively met by only one aspect of the embodiments discussed. Accordingly, it is not intended that the invention be limited, except as by the appended claims.

What is claimed is:

1. A variable stiffness optical fiber shaft for use in interventional therapy, comprising:
    an optical fiber having a proximal end and a distal end;
    a shape memory collar attached over said distal end of said optical fiber;
    a distal sheath connected to said distal end of said optical fiber and extending over a portion of said shape memory collar;
    a reinforcing tube attached to said optical fiber, said optical fiber extending therethrough;
    a reinforcing braid attached over said optical fiber and over a distal portion of said reinforcing tube;
    at least one layer of heat shrink material attached over said reinforcing tube, said reinforcing braid, and said optical fiber, to thereby provide a composite shaft with variable stiffness along its length.

2. The variable stiffness optical fiber shaft of claim 1, further comprising a radiopaque marker attached to said optical fiber.

3. The variable stiffness optical fiber shaft of claim 2, wherein said radiopaque marker is attached to said distal portion of said optical fiber.

4. The variable stiffness optical fiber shaft of claim 3, wherein said radiopaque marker comprises a platinum wire coil.

5. The variable stiffness optical fiber shaft of claim 1, wherein said optical fiber comprises a covering of an outer buffer, and wherein said outer buffer is removed from a distal portion of said optical fiber.

6. The variable stiffness optical fiber shaft of claim 1, further comprising a connecting hub attached over a proximal portion of said optical fiber.

7. The variable stiffness optical fiber shaft of claim 6, wherein said connecting hub is attached over said proximal portion of said optical fiber with adhesive.

8. The variable stiffness optical fiber shaft of claim 6, further comprising a strain relief member attached over said proximal portion of said optical fiber.

9. The variable stiffness optical fiber shaft of claim 1, wherein said reinforcing tube has at least one taper ground onto said reinforcing tube along its length.

10. The variable stiffness optical fiber shaft of claim 1, wherein said reinforcing tube comprises a metal hypo tube bonded to said optical fiber over at least a portion of its length.

11. The variable stiffness optical fiber shaft of claim 10, wherein said hypo tube is tapered along its length.

12. The variable stiffness optical fiber shaft of claim 1, further comprising a reinforcing coil attached over said optical fiber and under a distal portion of the reinforcing tube.

13. The variable stiffness optical fiber shaft of claim 1, further comprising a strain relief member attached over said proximal portion of said optical fiber.

14. The variable stiffness optical fiber shaft of claim 1, wherein said reinforcing braid is formed of stainless steel.

15. The variable stiffness optical fiber shaft of claim 1, wherein said shape memory collar is attached over said distal end of said optical fiber by adhesive.

16. The variable stiffness optical fiber shaft of claim 1, wherein said distal sheath is formed of polyethylene.

17. The variable stiffness optical fiber shaft of claim 1, wherein said distal sheath is formed from said at least one layer of heat shrink material over said distal end of said optical fiber.

18. A method of constructing a variable stiffness optical fiber shaft comprising the steps of:
    providing an optical fiber, said optical fiber having a proximal end and a distal end;
    attaching a shape memory collar over said distal end of said optical fiber;
    attaching a distal sheath formed of said heat shrink material over said distal end of said optical fiber, said distal sheath extending over a portion of said shape memory collar;
    attaching a reinforcing tube to a proximal portion of said optical fiber, said optical fiber extending through said reinforcing tube;
    applying a reinforcing braid over a middle to distal portion of said optical fiber;
    shrinking at least one layer of heat shrink material over said reinforcing tube, said reinforcing braid, said radiopaque marker, and said optical fiber, to thereby provide a composite shaft with variable stiffness along its length.

19. The method of claim 18, further comprising the step of attaching a radiopaque marker to a distal portion of said optical fiber.

20. The method of claim 19, wherein said radiopaque marker comprises a platinum coil.

21. The method of claim 18, wherein said step of applying a reinforcing braid comprises disposing a proximal portion of said reinforcing braid over a distal portion of said reinforcing tube.

22. The method of claim 18, wherein said optical fiber is covered with an outer buffer, and further comprising the step of removing said outer buffer from a distal portion of said optical fiber.

23. The method of claim 18, further comprising the step of attaching a connecting hub over a proximal portion of said optical fiber.

24. The method of claim 23, wherein said step of attaching a connecting hub comprises bonding said connecting hub over a proximal portion of said optical fiber with adhesive.

25. The method of claim 18, further comprising the step of attaching a strain relief member over said proximal portion of said optical fiber.

26. The method of claim 18, wherein said step of attaching a reinforcing tube to said optical fiber comprises providing said reinforcing tube with at least one taper into along its length.

27. The method of claim 18, further comprising the step of applying a reinforcing coil over said optical fiber.

28. The method of claim 27, wherein said step of applying a reinforcing coil comprises applying said reinforcing coil over a distal portion of said optical fiber and under a distal portion of said reinforcing tube.

29. The method of claim 18, wherein said step of attaching a shape memory collar comprises bonding said shape memory collar to said distal end of said optical fiber with adhesive.

30. The method of claim 18, wherein said step of attaching a distal sheath comprises attaching a distal sheath formed from a material selected from the group consisting of polyethylene, polytetrafluoroethylene, and polyethylene terephthalate over said distal end of said optical fiber and over a portion of said shape memory collar.

* * * * *